(12) United States Patent
Matsumoto et al.

(10) Patent No.: US 7,400,406 B2
(45) Date of Patent: Jul. 15, 2008

(54) MICROCHIP MEASUREMENT DEVICE

(75) Inventors: Shigeki Matsumoto, Himeji (JP); Toru Koshindo, Himeji (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 195 days.

(21) Appl. No.: 11/459,767

(22) Filed: Jul. 25, 2006

(65) Prior Publication Data
US 2007/0019184 A1 Jan. 25, 2007

(30) Foreign Application Priority Data
Jul. 25, 2005 (JP) ............................. 2005-214789

(51) Int. Cl.
*G01N 21/00* (2006.01)
(52) U.S. Cl. ...................... 356/434; 356/432
(58) Field of Classification Search .......... 356/432–444
See application file for complete search history.

(56) References Cited

U.S. PATENT DOCUMENTS

| | | | |
|---|---|---|---|
| 4,602,193 A | 7/1986 | Patonay et al. | |
| 5,485,061 A | 1/1996 | Ukita et al. | |
| 5,548,661 A | 8/1996 | Price et al. | |
| 5,716,852 A * | 2/1998 | Yager et al. | 436/172 |
| 5,948,684 A * | 9/1999 | Weigl et al. | 436/52 |
| 6,130,748 A * | 10/2000 | Kruger et al. | 356/450 |
| 6,224,830 B1 * | 5/2001 | Harrison et al. | 422/82.11 |
| 2002/0045272 A1* | 4/2002 | McDevitt et al. | 436/518 |
| 2005/0006372 A1 | 1/2005 | Murakami et al. | |
| 2005/0136548 A1* | 6/2005 | McDevitt et al. | 436/180 |

FOREIGN PATENT DOCUMENTS

| | | |
|---|---|---|
| JP | 2003-107094 A | 4/2003 |
| JP | 2004-109099 A | 4/2004 |

\* cited by examiner

*Primary Examiner*—Gregory J. Toatley, Jr.
*Assistant Examiner*—Jarreas C Underwood
(74) *Attorney, Agent, or Firm*—David S. Safran (57) ABSTRACT

A microchip analysis device in which the effect of changes in the quantity of light of a discharge lamp of the short arc type can be reduced and measurement results with high reliability can be obtained is achieved in microchip measurement device which has a light source lamp and a lamp operating device, in which the light from the lamp is transmitted by a fill part for the liquid of the microchip to be tested, and in which the quantity of this transmitted light and based on the data obtained the decadic extinction of the liquid to be tested are measured, a device determines the fluctuation of the quantity of light from the light source lamp. Based on data from this device, a control interrupts or stops the detection of the quantity of the light transmitted by the microchip when the fluctuation is outside a preset range.

3 Claims, 7 Drawing Sheets

MICROCHIP MEASUREMENT DEVICE

BACKGROUND OF THE INVENTION

1. Field of the Invention

The invention relates to a microchip measurement device.

2. Description of Related Art

In various fields such as medical treatments, biology and the like, a process has recently been under increasing development which is called μ-TAS (μ-Total Analysis System) or "Lab on a chip" and in which analyses are performed with high precision and high sensitivity using a microchip and substances are synthesized with high efficiency. For example, μ-TAS is a device in which chemical processes such as pumping, mixing, injections, reactions, extractions, analyses and the like are integrated into one microchip. Since this device can carry out chemical reactions which cannot be performed in chemical facilities with ordinary scales, with high efficiency, it has a potential to become an important tool for carrying out everyday health check-ups and injections and therapies with consideration of different individual body compositions.

In a microchip analysis system, to measure the concentration of a component to be detected in a test object liquid (hereinafter also called "liquid to be tested"), generally a process for analysis of decadic extinction [i.e., absorbance] is used.

In an analysis of decadic extinction, based on the obtained decadic extinction, the concentration of the component to be detected in the liquid to be tested is computed. Such a microchip measurement device is described, for example, in Japanese patent disclosure document JP 2004-109099 A.

In the above described microchip analysis system, the wavelength range of the radiated light differs according to the component to be analyzed. Therefore, in the case of a light source which emits a single wavelength, such as a laser, the substance to be analyzed is limited. In order to achieve versatility, it is advantageous to use a light source which can change the wavelength of the light to be emitted according to the substance to be analyzed and which emits light with a wide wavelength range.

Therefore, a lamp can be imagined as the light source which, for example, emits light with a wide emission spectrum. In particular, a short arc lamp is also advantageous with respect to the focusing property since it has high radiance and is a point light source.

Figure 8:
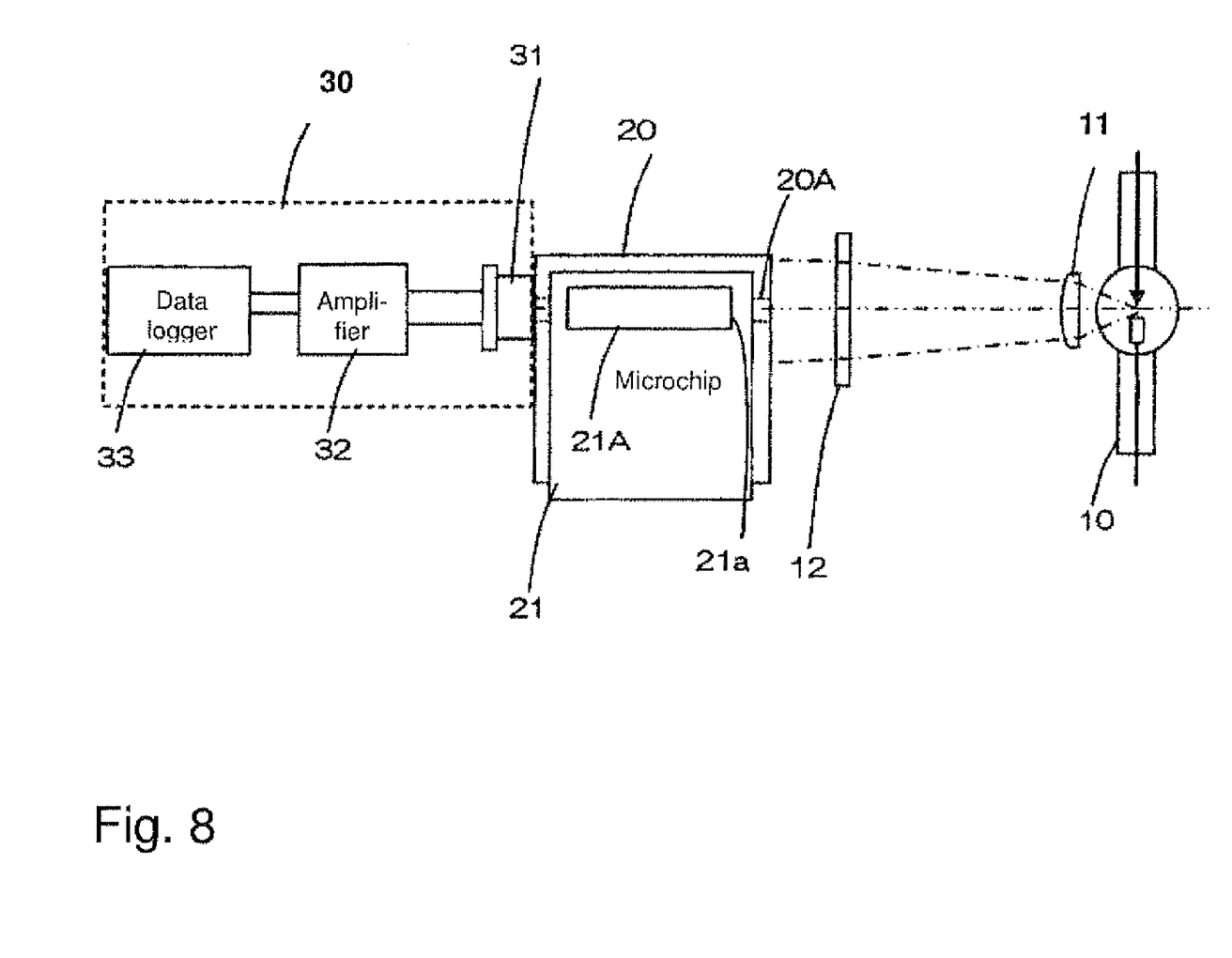
FIG. 8 is a schematic of the optical system of a microchip analysis system.

FIG. 8 schematically shows the optical system of a microchip analysis system. In the figure, a short arc lamp 10 emits light that is converted via given optical elements 11, 12 into parallel light, moreover, with wavelengths being extracted only in a given range and being incident in a chip holder 20. The light incident in the chip holder 20 passes through an aperture 20A and is incident in the incidence surface 21a of the measurement part 21A of the microchip 21. The light which is transmitted by the liquid which is to be tested and with which the measurement part 21A is filled is incident in a photodiode 31 as a light receiving element. An amplifier 32 is connected to the light receiving element 31. The data, after amplification of the light quantity, are recorded in a recording means, such as a data logger 33 (automatic recording means or the like). After a given measurement interval has passed, in an operation part (not shown), measurement data are analyzed and the decadic extinction is computed. The data of the quantity of light are determined by a control element (not shown) during a given decadic extinction measurement interval, for example, with an interval of 1 second.

(Patent document 1) Japanese patent disclosure document 2004-109099

(Patent document 2) Japanese patent disclosure document 2003-107094

(Patent document 3) Japanese patent disclosure document 2005-040784 corresponding to U.S. Patent Application Publication US2005006372.

In a discharge lamp of the short arc type, there are cases in which the phenomenon of an arc jump occurs towards the end of the lamp service life. When the phenomenon of an arc jump occurs, the position of the arc formed between the electrodes fluctuates. When an arc jump occurs, the flow of thermions which have flowed in the same path region temporarily changes its path region, by which resistances and the voltage shift and the quantity of light are likewise increased or reduced. When arc jump occurs, and the quantity of light emitted from the lamp does not stabilize, even for a small change in the quantity of light major influences are exerted on the measurement of the microchip because the cross-sectional area of the light incidence part which is formed in the microchip is, for example, 1 mm×1 mm, i.e., is extremely small.

As a correction means, it can be imagined that the fluctuation between the quantity of light prior to light incidence in the microchip and the quantity of light after passage (light exit) is monitored. Since control of the optical axis is very difficult in practice and in addition costs are high, implementation is however difficult.

SUMMARY OF THE INVENTION

Therefore, a primary object of the present invention is to devise a microchip analysis device in which, with a relatively simple arrangement, the effect of increasing or decreasing the quantity of light of a discharge lamp of the short arc type can be reduced and in which thus measurement results with high reliability can be obtained.

The object is achieved in accordance with the invention in a microchip measurement device which has a light source lamp and a lamp operating device for operation of the light source lamp, in which the light from the lamp is transmitted by a fill part for the liquid of the microchip to be tested, and in which the quantity of this transmitted light, and based on the data obtained, the decadic extinction of the liquid to be tested are measured, by the following features:

a means for determining the quantity of light from the lamp, which determines the fluctuation of the quantity of light from the light source lamp; and a control means which, based on data from the means for determining the quantity of light from the lamp, interrupts or stops the detection of the quantity of the light transmitted by the microchip in the case of determining the fluctuation.

Furthermore, the object is achieved in that the above described lamp operating device is driven using a constant current, that the above described means for determining the quantity of light from the lamp is comprised of a lamp voltage determination circuit which, based on the fluctuation of the operating voltage of the above described light source lamp, determines the light quantity fluctuation, and that the above described control means compares the data of the lamp voltage determination circuit with a preset, given value and exercises control such that the detection of the quantity of the light transmitted by the microchip is interrupted in case these data are outside of a given range.

The object is also achieved in that the above described lamp voltage determination circuit comprises a constant voltage generating power source for generating a reference voltage, and an amplifier.

The object is, moreover, achieved in that the above described means for determining the quantity of light from the lamp is comprised of a light receiving element for direct reception of the light emerging from the above described light source lamp and that the above described control means compares the data of the quantity of light from the above described light receiving element to a preset, given value and temporarily stops the measurement of the quantity of light transmitted by the microchip when these data are outside a given range.

ACTION OF THE INVENTION

In accordance with the invention the following effects are obtained:

(1) By exercising control such that the detection of the quantity of light transmitted by the microchip in the case of determining the fluctuation in the arc is interrupted or stopped, effects due to the fluctuation of the quantity of lamp light on the measurement of decadic extinction can be prevented. A microchip measurement device can be devised in which the decadic extinction is measured with high precision and results with high reliability can be obtained.

(2) In the case in which the lamp operating device is driven using a constant current, by determination of the arc fluctuation by determining the voltage fluctuation the above described device can be implemented with a relatively simple circuit arrangement.

(3) The light transmitted by the microchip can be determined in real time by the arrangement of a light receiving element for direct determination of the quantity of light of the lamp independently of the light receiving element for determining the light transmitted by the microchip and by determining the arc fluctuation.

(4) By determining the arc fluctuation, the lamp service life can be predicted. The lamp can be replaced without missing the opportunity and the reliability of the determination results can be kept high by the microchip measurement device.

The invention is further described below with reference to the accompanying drawings.

DETAILED DESCRIPTION OF THE INVENTION

Figure 1:
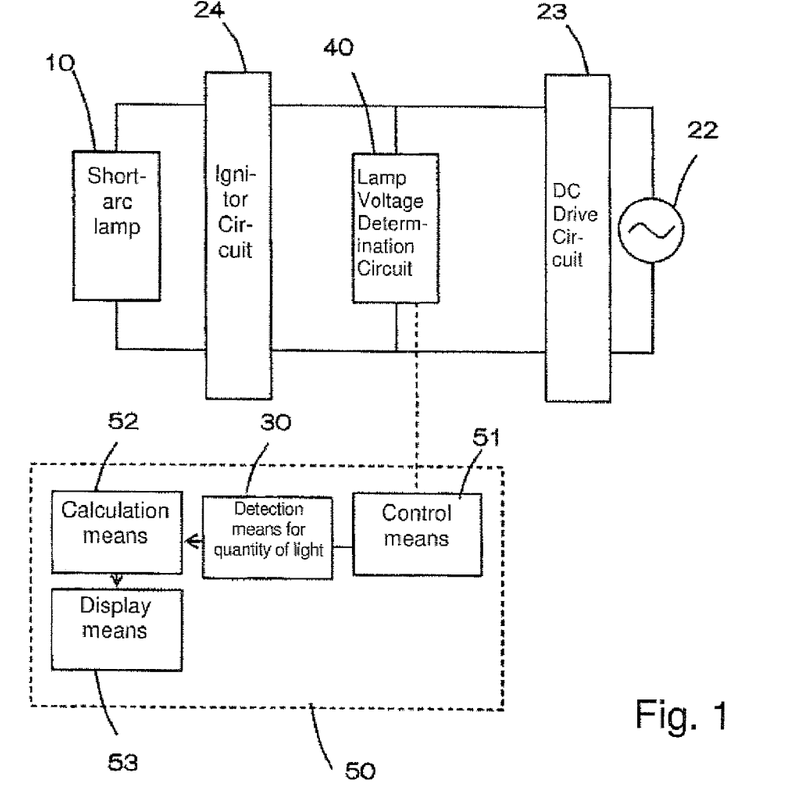
FIG. 1 is a block diagram of the arrangement of the microchip measurement device in accordance with the invention.
Figure 2:
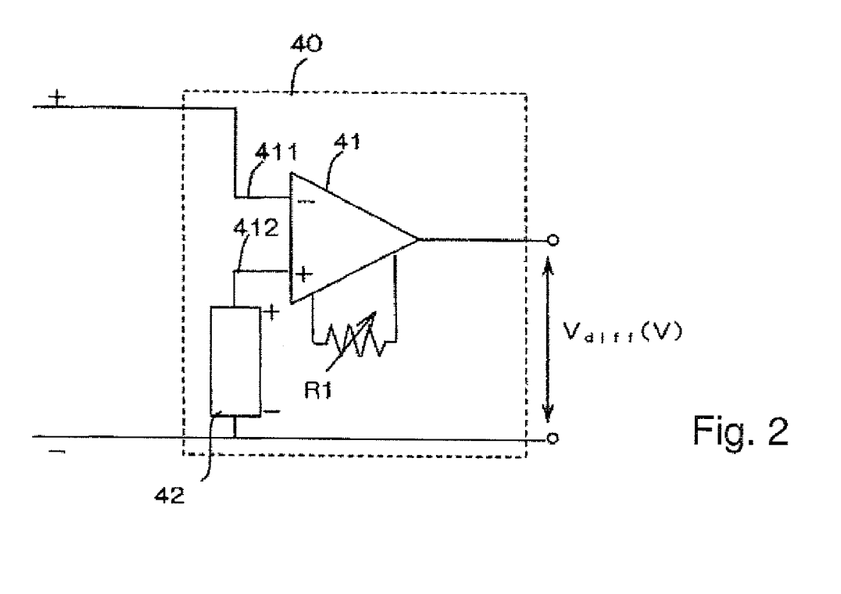
FIG. 2 is a schematic of the circuit arrangement of one example of a means for determining the arc fluctuation.
Figure 3:
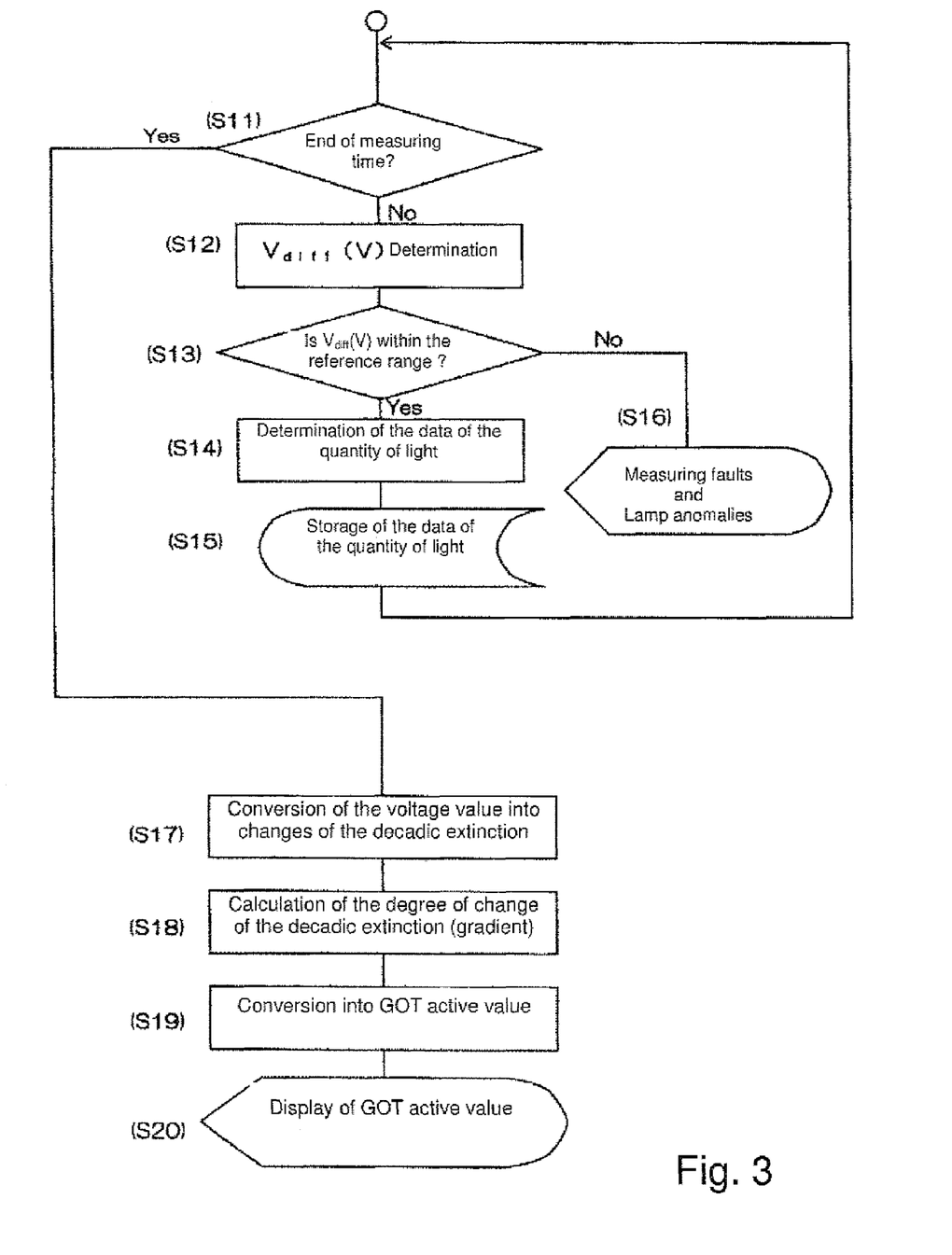
FIG. 3 is a flowchart of the measurement sequence of a microchip in accordance with the invention.
Figure 4:
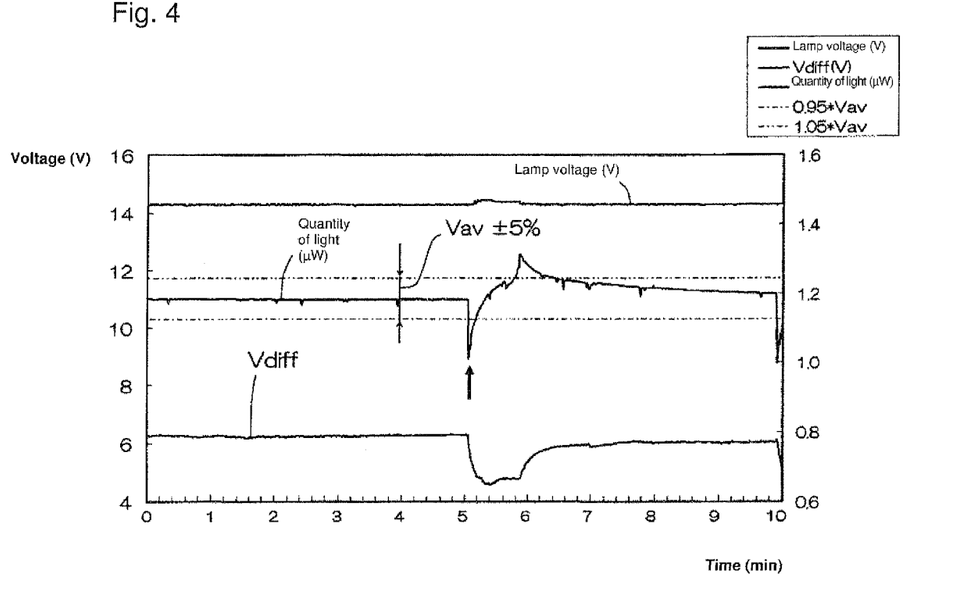
FIG. 4 is a sample time chart which shows the quantity of measured light and the lamp voltage.

FIG. 1 is a block diagram of the microchip measurement device in accordance with the invention. FIG. 2 shows an example of a circuit arrangement of a means for determining the arc fluctuation. FIG. 3 shows a flowchart of the invention. FIG. 4 shows an example of a time chart of the arc determination means. Since in the microchip measurement device the arrangement of the optical system is identical to the above described arrangement as shown in FIG. 8, it is described using it.

The microchip measurement device according to this exemplary embodiment measures the concentration of the component to be detected in a liquid which is to be tested (test object) and with which the microchip is filled, by a process for analysis of decadic extinction. For example, GOT active values are measured in this process.

In FIG. 1, a direct current driver circuit converts the power from a line current source into a direct current and exercises constant current control.

In the figure, a short arc lamp 10, which is for example a xenon lamp, comprises tungsten electrodes in a silica glass bulb to which xenon gas is added. The distance between the electrodes is 0.7 mm, the rated power consumption is 75 W and the rated voltage (Vr) is 14.3 V.

The xenon lamp yields high irradiance, and moreover, a point light source is easily obtained. A stable emission spectrum is obtained which, in a wide wavelength range from 250 nm to 1400 nm, has a continuous spectrum and in which, in the wavelength range which is often used to measure decadic extinction (specifically, in the wavelength range from 300 nm to 800 nm), a strong emission line is not formed.

An igniter circuit 24 is located on the tip of the direct current driver circuit 23. The starting high voltage produced here is applied to the short arc lamp.

The light emitted by the short arc lamp 10 is converted into parallel light by optical elements 11, 12 that are arranged as shown in FIG. 8, and only wavelengths in a given range are extracted and are incident in a chip holder 20. The light incident in the chip holder 20 passes through an aperture 20A and is incident in the incidence surface 21a of the measurement part 21A of the microchip 21.

A lamp voltage determination circuit 40 which determines the fluctuation of the lamp voltage is connected to the direct current driver circuit 23 as a means for determining the quantity of lamp light. The lamp voltage determination circuit 40 is specifically formed of the circuit shown in FIG. 2.

In FIG. 2, there is an instrument amplifier 41 for a differential determination. A terminal 411 is connected to the terminal on the plus (+) side of the lamp, while the other terminal 412 is connected via a reference voltage generating power supply to the terminal on the minus (−) side of the lamp.

The reference voltage generating power source 42 is comprised of a constant voltage generating power source and generates a voltage which has approached the rated voltage of the short arc lamp 10. The instrument amplifier 41 amplifies the difference and sends an amplified value $V_{diff}(V)$ to the microchip measurement means 50 when a voltage value is detected which is obtained by the (lamp voltage $V_L$−reference voltage value of the reference voltage generating power source 42) by a resistance R1 for controlling the differential gain with a given sensitivity factor.

The microchip measurement means 50, as is shown using the block diagram in FIG. 1, comprises a control means 51, a measurement light quantity determination part 30, a calculation means 52, and a display means 53. The voltage value from the lamp voltage determination circuit 40 which has been sent to the microchip measurement means 50 is processed in the control means and when this value is outside a predetermined, given range sends a signal to the measurement light quantity determination part 30 which indicates that the data of the quantity of light can be acquired. When the detected value deviates from a given range, it is assessed that an arc fluctuation has occurred and the measurement of the decadic extinction is interrupted. Furthermore an indication is sent to the display means 53 in order to show "measurement errors".

The given range which is set by the control means is fixed in that the data of the voltage amplification value $V_{diff}(V)$ for example during the minute between ten minutes having passed and eleven minutes having passed after the start of operation of the lamp are brought to an average and a range of ±5% of this value $V_{diff}(V)$ is regarded as a stipulated range.

A photodetector means 52, which comprises, for example, the measurement light quantity determination part 30 shown in FIG. 8 (i.e., the light receiving element 31, an amplifier 32, a data logger 33) and which determines the quantity of light based on the indication of the detection of the data of the light quantity from the control means 51 shown in FIG. 1. The light receiving device 31 comprises, specifically, a silicon photodiode which is a light receiving element with a sensitivity to light in the wavelength range from 300 nm to 1100 nm and which receives the transmitted light by the measurement part 21A of the microchip 21 and converts it into a voltage value. The data logger 33 records the voltage value which has been amplified by the amplifier 32 and the clock time of the light quantity measurement and stores it.

If it is assessed by the control means 51 shown in FIG. 1 that the given interval of measurement of decadic extinction has expired, the voltage data determined by the photodetector means 52 and stored are output to the calculation means 52.

The calculation means 52, based on the voltage data, computes the degree of change of the decadic extinction (gradient) and converts it into difference values based on a preset operation formula. Afterwards the received values are displayed in the display means 53.

In this case of determination of the fluctuation of the lamp voltage, i.e., when an arc jump and flicker form, the measurement of the quantity of light is interrupted, which enables measurement results with high reliability to be obtained.

FIG. 3 is a flow chart of the operating sequence of this embodiment. The operating sequence of the invention is described using FIGS. 1, 3 & 8.

1. When preparation for the measurement of the lamp 10 and of the microchip 21 is completed, the measurement is started by a manual switch actuation. The duration of the measurement of decadic extinction is preset. In the case of detection of a GOT active value, the duration of the measurement of decadic extinction is, for example, roughly 10 minutes.

2. The control means 51 assesses whether the given measurement interval has expired or not (step S11). When a voltage is present during the measurement interval, the control means 51 of the lamp voltage determination circuit 40 gives a command to detect $V_{diff}(V)$.

3. When $V_{diff}(V)$ is detected (step S12), the lamp voltage determination circuit 40 sends this value to the control means 51. The control means 51 compares $V_{diff}(V)$ to a preset, given value (step S13) and gives an indication, when they lie within a given range, to the measurement light quantity determination part 30 to detect the data of the quantity of light.

4. The measurement light quantity determination part 30 determines the data of the quantity of light (step S14) and stores them (step S15). After storage of the data of the quantity of light, there is a return to the initial step S11. If the measurement interval is still running, the actuations from step S11 to step S15 are repeated. The detection interval of $V_{diff}(V)$ data is, for example, 1 second. If there is no fluctuation of $V_{diff}(V)$, the quantity of light is determined each second.

5. If, in step S13, $V_{diff}(V)$ deviates from the pre-established given range, the display means 53 displays "measurement errors", by which lamp replacement is accelerated, and moreover, measurement of the decadic extinction is interrupted.

6. If, in step S11, the given measurement interval is expiring, the data stored in the measurement light quantity determination part 30 is sent to the calculation means 52.

7. The calculation means 52 converts the voltage value which was obtained as the data of the quantity of light into the decadic extinction (step S17), and furthermore, based on this computes the degree of change of the decadic extinction (gradient) (step S18), based on which conversion is performed by a pre-established operation formula into the GOT active value (step S19). The GOT active value obtained is displayed by the display means 53 (step S20).

FIG. 4 shows by way of example a time chart of the quantity of light (μW) and the voltage (V) at the incidence surface 21a of the microchip 21. The curves in the figure represent the actual lamp voltage (V), the amplified voltage data $V_{diff}(V)$ and the quantity of light (μW). After ten minutes of lamp operation have passed, the voltage data $V_{diff}(V)$ are measured for one minute, their average is computed and the range ±5% of this value is established as a given range ($V_{av}$±5% range). After determining the given range, measurement of the quantity of light quickly began, and the data were acquired for 10 minutes. In this example the reference voltage $V_S(V)$ which forms in the reference voltage generating power source is 14.6 V and the difference was amplified by a factor of 20.

The absolute value of the difference between the rated voltage $V_r(V)$ and reference voltage $V_s(V)$ is |14.3−14.6|=0.3 (V). The voltage data $V_{diff}(V)$ of the lamp voltage $V_L(V)$, in this example, are therefore plotted roughly at 0.3×20=6 (V).

If the above described computation formula is generalized, the differential amplification voltage is described as follows:

Differential amplification voltage: $V_{diff}$=|lamp voltage−reference voltage value $V_{ref}$|×amplifier gain In the example in FIG. 4, roughly five minutes after the measurement begins, a fluctuation of the quantity of light (shown using the bold arrow) arises. Starting at this instant, the gradient of the voltage data $V_{diff}(V)$ changes and decreases such that the line from $V_{av}$−5% is far from reached. This is apparently due to the following:

In such a case of a change of the lamp voltage and deviation of this value from the range of $V_{av}$±5%, a fluctuation of the quantity of light, such as an arc jump, flicker, or the like has occurred.

Furthermore, as becomes apparent from this time chart, for the lamp voltage data, the peak fluctuation value of the quantity of light does not agree with the peak value of the voltage, so that it is difficult to assess detection or nondetection of the quantity of light in real time. In the case of determining the fluctuation of the quantity of light by the lamp voltage fluctuation, it is therefore desirable, at the instant of determination of the anomaly, to interrupt the measurement of the decadic extinction and to replace the short arc lamp as a light source, and the microchip.

The reason for amplifying the difference between the lamp voltage and the reference voltage in determining an extremely small change of the lamp voltage for the above described embodiment is the following.

The measurement and processing of the voltage are normally carried out digitally. When the voltage change is extremely small and when a change occurs in the range of less than the effective place number of the measurement means of the voltage, it is possible to overlook it. When the effective place number of the measurement means of the voltage is, for example, 6 or 7, and when this measurement means can measure even extremely small changes with high resolution, amplification is not necessary. Arranging such a voltmeter with high efficiency, however, only leads to an unrealistic increase in the cost of the device.

The amplification in accordance with the invention before digital processing of the acquired voltage, i.e., in an analog step, can therefore be performed with relatively low costs. Furthermore, by detecting the difference between the voltage and the reference value, superfluous numerical values with high place numbers can be avoided in the determination of an extremely small fluctuation, and thus, even extremely small changes can be determined.

Especially for a short arc lamp which is used for a microchip determination device, the rated power consumption is, for example, 50 W to 75 W and the lamp voltage is, for example, 12 V to 15 V. The voltage fluctuation by an arc jump or flicker does not reach even 1% of the lamp voltage, i.e., it is therefore extremely small. Determination of a fluctuation of less than 0.1 V with respect to a lamp voltage of ten and some volts is extremely difficult. By detecting the difference between the lamp voltage and the reference voltage and by amplification, it becomes possible to determine even a small voltage shift of the lamp with high precision, as was described above. Therefore, the means in accordance with the invention by which the fluctuation of the lamp voltage is amplified and the voltage data $V_{diff}(V)$ are determined enables an extremely small voltage fluctuation resulting from an arc fluctuation to be determined with certainty.

In the above described arrangement, the reference voltage value which arises in the reference voltage generating power source can be set roughly at the rated voltage of the lamp, as was described above. Since, in the short arc lamp, in the course of its use, the electrodes wear and the pole distance increases, there is the tendency for the lamp voltage to gradually rise. In practical use it is, therefore, advantageous in each measurement of the decadic extinction to correct the reference voltage value which forms in the reference voltage generating power source and accordingly to acquire the voltage data $V_{diff}(V)$.

Reference voltage value $V_{ref}$=average value of the voltage during the minute after between ten and eleven minutes have passed after the start of lamp operation.

The reason for detecting the voltage after ten minutes of lamp operation have passed is that immediately after the start of lamp operation, the lamp arc is unstable and the fluctuation of the voltage value is great, and after ten minutes have passed a voltage value in the stable state can be determined.

By the above described invention, the arc fluctuation of a short arc lamp based on the voltage value is determined, and when an arc fluctuation occurs the quantity of light which has been transmitted by the microchip is not measured. In this way, when an increase or decrease of the quantity of light occurs due to arc fluctuation, an unnecessary measurement is avoided and the desired measurement can be taken on the microchip with high precision.

Furthermore, since, together with determination of the arc fluctuation based on the voltage value, the formation or nonformation of the arc fluctuation is assessed using its amplification value, fluctuations can also be determined which are still smaller than the determination limit of the voltmeter, and it can be reliably ascertained that an arc fluctuation has occurred.

Figure 5:
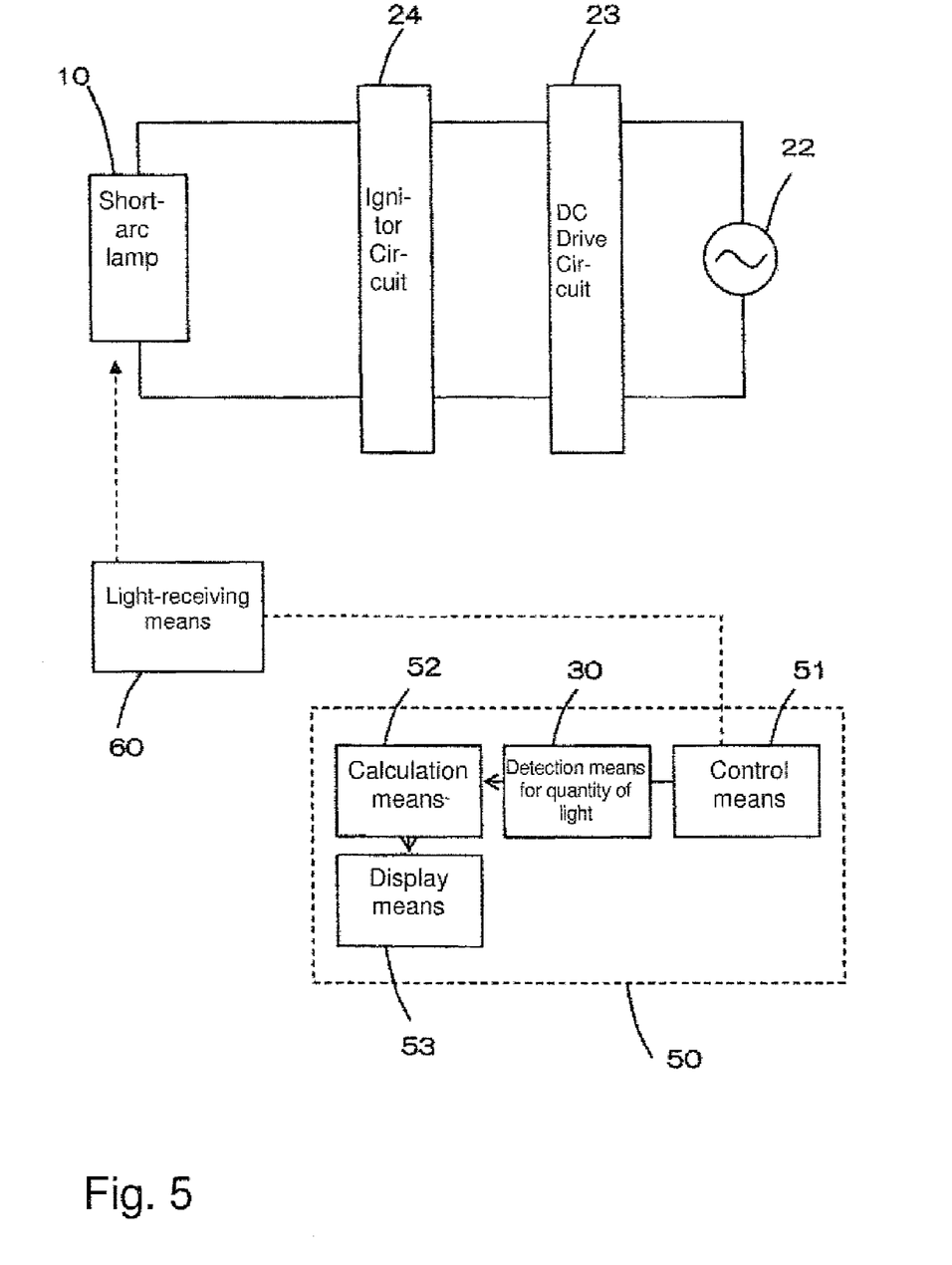
FIG. 5 is a schematic block diagram in the case of determining the arc fluctuation by an arrangement of a light receiving device for monitoring the fluctuation of the quantity of light according to another embodiment of the invention.
Figure 6:
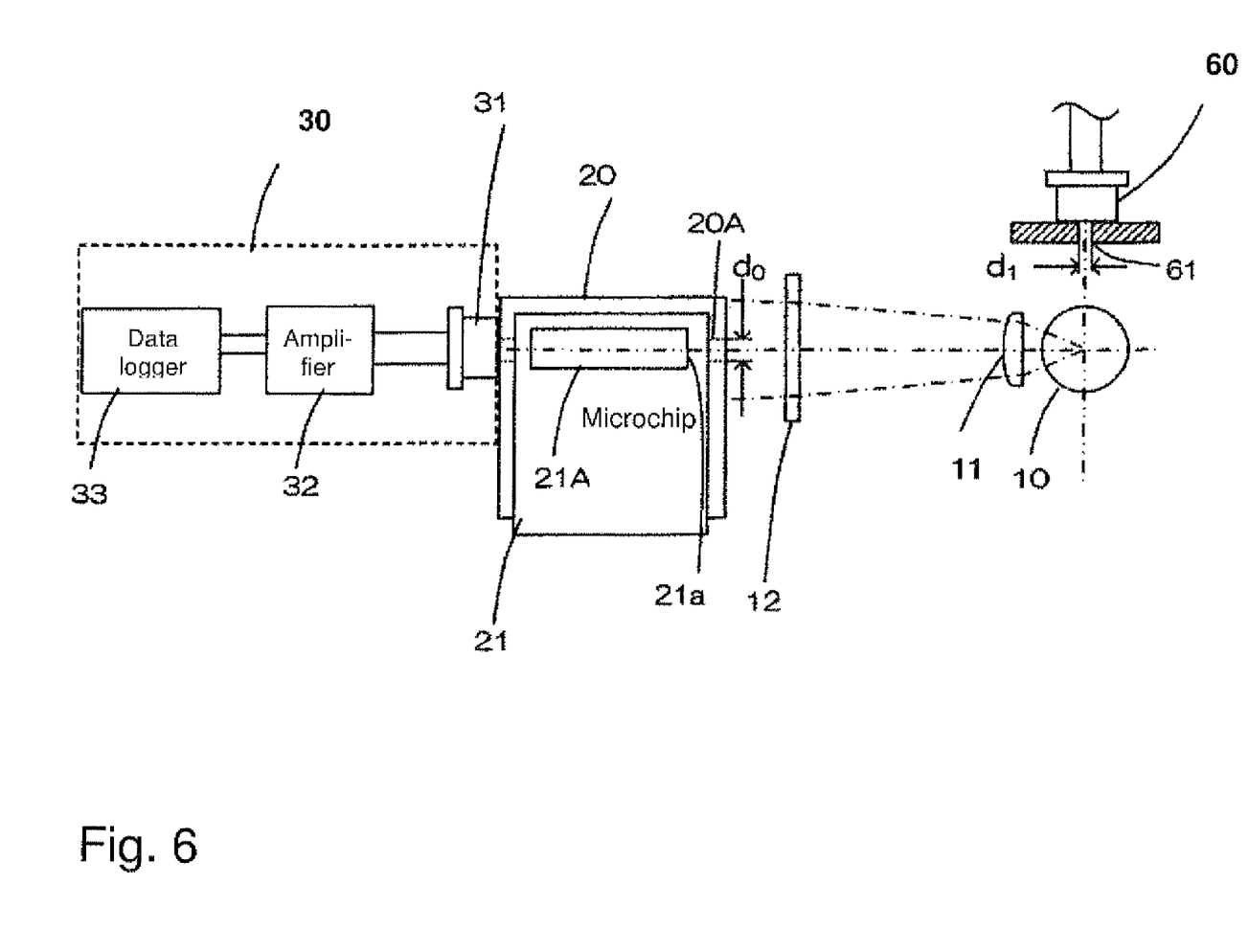
FIG. 6 is a schematic of the arrangement of the optical system according to another embodiment of the invention.

Another embodiment of the invention is described below which differs from the above described embodiment. FIG. 5 shows a schematic block diagram in the case in which there is a light receiving device for monitoring the fluctuation of the quantity of light and in which the arc fluctuation is determined. FIG. 6 is a schematic of the arrangement of the optical system. In FIGS. 5 & 6, the same parts as in FIGS. 1 & 8 are provided with the same reference numbers and are not further described.

This embodiment differs from the above described embodiment in that, as the means for determining the quantity of light of the lamp, instead of a lamp voltage determination circuit, there is additionally a light receiving element 60 for monitoring the light emerging from the lamp. The light receiving element 60 for determining the arc fluctuation is used to monitor the arc fluctuation in the lamp and comprises, specifically, a silicon photodiode. The silicon photodiode used as the light receiving element 60 in this connection, specifically, has a sensitivity to light in the wavelength range from 300 nm to 1100 nm, receives light which has passed through an aperture 61 which is located directly in front, converts the data of the quantity of light into a voltage value, and send these data to the microchip measurement means 50 shown in FIG. 5. The aperture 61 chokes the light from the short arc lamp 10 such that the light receiving element 60 is opposite the middle of the short arc lamp 10. Because, when the light is received by the light receiving element 60, the quantity of light is reduced to a certain extent by the aperture 61, an extremely small light quantity fluctuation can be determined without a special optical system being located between the short arc lamp 10 and the aperture 61.

In the case, for example, that the light receiving element 60 for determining the arc fluctuation is formed from a photodiode with a detection capacity to the same extent as the photodiode 31 for determining the light transmitted by the microchip 21, it is advantageous to have the intensity of the light incident in each of the light receiving elements 31, 60 approach one another. Therefore, it is also advantageous to make the opening diameter $d_1$ (mm) of the aperture 61 smaller than the opening diameter $d_0$ (mm) of the aperture 20A formed in the chip holder 20 and to reduce the quantity of light.

After detection of the data of the quantity of light which have been determined by the light receiving element 60 for monitoring the arc fluctuation, the microchip measurement means 50 collates these data in the control element with respect to whether they are within a pre-established range of the fluctuation of the quantity of light, and it assesses whether detection of the light transmitted by the microchip is possible or not. The range of fluctuation of the quantity of light meant here is fixed by the average value of the data of the quantity of light during the minute occurring between ten and eleven minutes having passed since the start of lamp operation being regarded as a reference value and ±5% thereof being regarded as the stipulated range.

When the data of the quantity of light acquired from the light receiving element 60 for monitoring the arc fluctuation are within a given range of the fluctuation of the quantity of light, an indication is given to the measurement light quantity determination part 30 that the quantity of light transmitted by the microchip is to be detected. On the other hand, in the case of a fluctuation beyond the given range, control is exercised such that the measurement light quantity determination part 30 is not to detect the quantity of light. Afterwards, if the quantity of light of the light receiving element 60 for monitoring the arc fluctuation falls in the given light quantity range, the detection of the quantity of light by the measurement light quantity determination part 30 is restarted.

Figure 7:
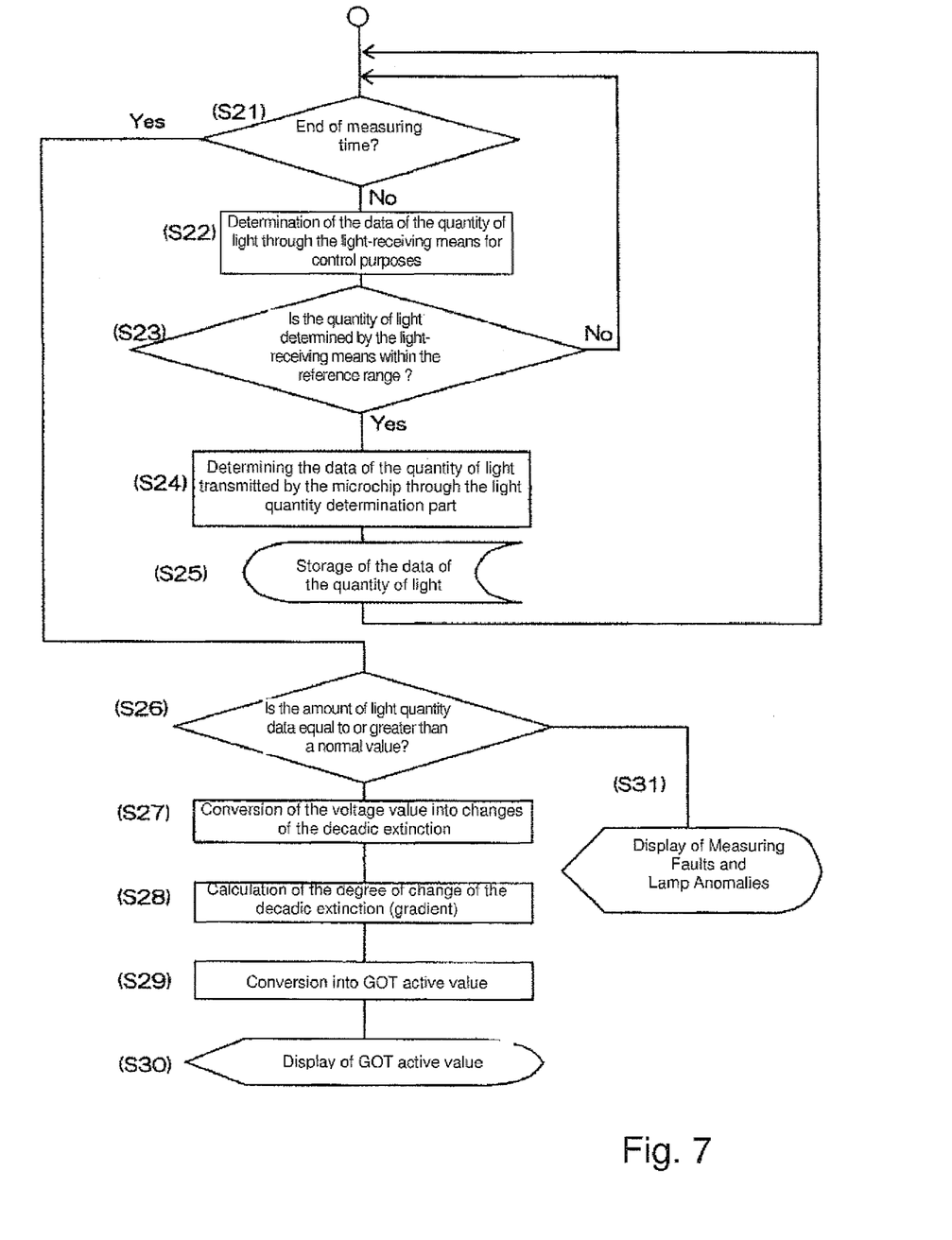
FIG. 7 is a flowchart for another embodiment of the invention.

FIG. 7 is a flowchart for this embodiment. This example also shows, as in the aforementioned embodiment, a case of determination of the GOT active values. Measurement of the decadic extinction takes, for example, roughly 10 minutes.

The operating sequence in this embodiment is described below using FIGS. 5 to 7.

1. When preparation for the measurement of the short arc lamp 10 and of the microchip 21 is completed, a measurement starting signal is sent to the control means 51 in the microchip measurement means 50 by automatic or manual switch actuation.

2. In the control means 51, it is assessed whether the given measurement interval has expired or not (step S21). When the measurement interval is found not to have expired, the control means 51 sends a command to detect the data of the quantity of light of the short arc lamp 10 to the light receiving element 60 for monitoring the arc fluctuation (photodiode).

3. When the light receiving element 60 for monitoring the arc fluctuation determines the data of the quantity of light (step S22), these data are sent to the control means 51. The control means 51 compares the obtained data of the quantity of light to a preset, given value (step S23) and gives an indication, when they lie within a given range, to the measurement light quantity determination part 30 to detect the data of the quantity of light which has been transmitted by the microchip 21.

4. For the measurement light quantity determination part 30, the light which has been transmitted from the microchip 21 is received by the photodiode 31 and the data of the quantity of light are acquired (step S24). The data of the quantity of light are stored in the data logger 33 (step S25). After storage of the data of the quantity of light, there is a return to the initial step S21. If the measurement interval has not expired, the same actuations from step S21 to step S25 are repeated. The detection interval of the data of the quantity of light for the light receiving element 60 for monitoring the arc fluctuation is, for example, 1 second. If no arc fluctuation is determined, synchronously thereto the quantity of light is also determined each second at the measurement light quantity determination part 30.

5. In the case in which, in step S23, the data of the quantity of light is outside the given range, the measurement light quantity determination part 30 does not detect the quantity of light, and there is a return to the initial step S1. If no deviation from the reference range is present during the given interval for measurement of the decadic extinction, steps S24 and S25 are performed and then steps 21 to 25 are repeated.

6. If in step S21 the given measurement interval is expiring, the data determined and stored in the measurement light quantity determination part 30 are sent to the calculation means 52. The calculation means 52 compares the data of the quantity of light to a pre-established value (step S26). When the value is greater than or equal to the established value, there is passage to the next step S27.

7. The operation part converts the voltage value which was obtained from the data of the quantity of light into the decadic extinction (step S27) and furthermore, based on this, computes the degree of change of the decadic extinction (gradient) (step S28), based on which conversion is performed by a pre-established operation formula into the GOT active value (step S29). The GOT active value obtained is displayed by the display means (step S30).

8. On the other hand, when the quantity of data of the quantity of light does not reach the established value in step 26, the data are faulty so that operation is impossible. In this case, the display means displays "measurement errors" (step S31).

In step S26, the lack of data of the quantity of light means a great fluctuation of the quantity of light. For example, in the case in which data are determined each second, during the interval for measurement of the decadic extinction (ten minutes, i.e., 600 seconds), the number of data is smaller than 8 (i.e., less than 480 seconds), it is assessed that the number of effective data is small and "error" is displayed (step S31). This means that an anomaly of the arc of the lamp often occurs and the lamp is at the end of its service life. Therefore, it is advantageous to also display, at the same time, a "lamp replacement warning alarm" by a display device or the like.

By the means in which the quantity of light in itself is determined by the light receiving device located in addition next to the lamp, in this way processing in real time can be performed so that no data need be collected during an arc fluctuation.

Embodiments of the invention were described above. However, the invention is not limited to the above described versions, and of course, various modifications and variations can be added. For example, the reference value voltage and the gain can be suitably established by resistances without limitation to the above described values. As a discharge lamp for a light source, besides a xenon lamp, also a super-high pressure mercury lamp, a metal halide lamp of the short arc type and the like, which are advantageously used as a light source of a projector device, can be used.

What we claim is:

1. Microchip measurement device, comprising:
   a fill part for a liquid to be tested;
   a light source lamp, light transmitted by the lamp being directed through the fill part for the liquid to be tested;
   a lamp operating device for operating the light source lamp;
   means for determining the quantity of light from the lamp, and for determining fluctuation of the quantity of light from the light source lamp based on data obtained as to the quantity of light from the lamp and measurement of the decadic extinction of the liquid to be tested; and
   control means for determining the quantity of lamp light based on data from the means for determining and for interrupting or stopping detection of the quantity of the transmitted when a fluctuation is determined; wherein the lamp operating device is driven by a constant current supply, wherein the means for determining the lamp light quantity comprises a lamp voltage determination circuit which, based on fluctuation of the operating voltage of the light source lamp, determines the light quantity fluctuation, and wherein the control means compares data of the lamp voltage determination circuit with a preset, given value and exercises control such that detection of the quantity of the light transmitted by the microchip is interrupted when said data are outside of a preset range.

2. Microchip measurement device in accordance with claim 1, wherein the lamp voltage determination circuit comprises a constant voltage generating power source for generating a reference voltage, and an amplifier.

3. Microchip measurement device in accordance with claim 1, wherein the means for determining the lamp light quantity comprises a light receiving element for direct reception of light emerging from the light source lamp, and wherein the control means compares data of the quantity of light from the light receiving element to a preset, given value and temporarily stops measurement of the quantity of light transmitted by the microchip when said data are outside a given range.

* * * * *